United States Patent [19]

Neumann et al.

[11] Patent Number: 4,996,354

[45] Date of Patent: Feb. 26, 1991

[54] PREPARATION OF 2,4-DIHYDROXYBENZOIC ACID

[75] Inventors: Peter Neumann, Mannheim; Ulrich Eichenauer, Frankfurt, both of Fed. Rep. of Germany

[73] Assignee: BASF Aktiengesellschaft, Ludwigshafen, Fed. Rep. of Germany

[21] Appl. No.: 401,941

[22] Filed: Sep. 1, 1989

[30] Foreign Application Priority Data

Sep. 21, 1988 [DE] Fed. Rep. of Germany ....... 3832076

[51] Int. Cl.$^5$ .............................................. C07C 51/15
[52] U.S. Cl. ................................... 562/424; 562/423
[58] Field of Search ................................ 562/423, 424

[56] References Cited

FOREIGN PATENT DOCUMENTS 9184146 10/1984 Japan .
734598 8/1955 United Kingdom .
734622 8/1955 United Kingdom .

OTHER PUBLICATIONS

The Journal of Organic Chemistry, vol. 19, 1954, pp. 510–514, Ogden Baine, et al., "A Study of the Kolbe–Schmitt Reaction, II., The Carbonation of Phenols".

Monatshefte Fur Chemie, vol. 81, 1950, pp. 1071–1091, F. Wessely, et al., "Zur Kenntnis Der Carboxylierung Von Phenolen".

Journal of Organic Chemistry, vol. 15, 1950, pp. 233–236, Don Cameron, et al., "The Kolbe–Schmitt Reaction. I. Variations in the Carbonation of p-Cresol".

Chemical Reviews, vol. 57, 1957, pp. 583–620, A. S. Lindsey, et al., "The Kolbe–Schmitt Reaction".

*Primary Examiner*—Paul J. Killos
*Attorney, Agent, or Firm*—Oblon, Spivak, McClelland, Maier & Neustadt

[57] ABSTRACT

2,4-Dihydroxybenzoic acid is prepared in a solids mixer by reacting resorcinol with an alkali metal bicarbonate and/or alklai metal carbonate in a carbon dioxide atmosphere using as the alkali metal bicarbonate or alkali metal carbonate a mixture of the corresponding sodium and potassium salts.

4 Claims, No Drawings

PREPARATION OF 2,4-DIHYDROXYBENZOIC ACID

The present invention relates to a novel process for preparing 2,4-dihydroxybenzoic acid in a solids mixer by reacting resorcinol with an alkali metal bicarbonate or carbonate in a carbon dioxide atmosphere, which comprises using as the alkali metal bicarbonate or carbonate a mixture of the corresponding sodium and potassium salts.

The preparation of benzoic acids by carboxylation in an alkali medium is known as a Kolbe synthesis. For resorcinol as the aromatic species the reaction in a solvent, which in general gives a poor yield and low selectivity, is not the only option because it is also possible to perform a Marassé solid-phase carboxylation with carbon dioxide in the presence of potassium carbonate (J. Org. Chem. 19, (1954) 510; Monatsh. 81, (1950) 1071; J. Org. Chem. 15, (1950), 233).

It is generally held that the Marassé reaction can only be carried out successfully using potassium, rubidium or cesium salts. The less costly sodium salts, by contrast, are held to be unsuitable (Chem. Rev. 57, (1957), 583).

It is an object of the present invention to provide a process for preparing 2,4-dihydroxybenzoic acid by solid-phase carboxylation using sodium bicarbonate or carbonate.

We have found that this object is achieved by preparing 2,4-dihydroxybenzoic acid in a solids mixer by reacting resorcinol with an alkali metal bicarbonate, alkali metal carbonate or a mixture thereof in a carbon dioxide atmosphere if the alkali metal bicarbonate or carbonate used is a mixture of the corresponding sodium and potassium salts.

The proportion of potassium salts in the mixture is in general from 10 to 60% by weight, preferably from 20 to 40% by weight, each percentage being based on the weight of the total of sodium and potassium salt.

Preference is given to using a mixture of sodium bicarbonate and potassium bicarbonate.

In principle it is also possible to carry out the reaction in the presence of sodium bicarbonate and/or sodium carbonate alone, but in that case a longer reaction time is required.

In general, from 400 to 1500 g, preferably from 450 to 700 g, in particular from 500 to 600 g, of the mixture of sodium bicarbonate and potassium bicarbonate and/or carbonate are used per mole of resorcinol.

The process according to the invention is advantageously carried out at from 80 to 140° C., preferably at from 100 to 120° C.

The carbon dioxide required for the reaction is preferably supplied to the reaction under atmospheric pressure. However, it is also possible to work under superatmospheric pressure, in general at up to about 20 bar. The carbon dioxide can also be diluted by inert gases, for example nitrogen, up to a pressure of 0.5 bar.

The reaction mixture may further contain inert substances, for example inorganic salts, for example halides, sulfates or phosphates of alkali metals or alkaline earth metals or even alkaline earth metal bicarbonates or alkaline earth metal carbonates, without adversely affecting the reaction. Furthermore, it is also possible to add inert materials such as minerals or metals. In general, the amount of inert substances added is from 0 to 200% by weight, preferably from 0 to 100% by weight, based on the reaction mixture.

The process according to the invention is carried out in a solids mixer. Such apparatus is known and described for example in Ullmanns Encyklopädie der Technischen Chemie, 4th edition, volume 2, pages 304–310.

The novel process is advantageously carried out by initially charging the solids mixer with the resorcinol and the mixture of sodium bicarbonate and potassium bicarbonate and/or carbonate with or without any of the abovementioned inert substances, and adding carbon dioxide under mixing conditions. Following heating to the abovementioned temperature and a reaction time of about 1 to 10 hours, preferably about 2 to 4 hours, under the abovementioned reaction conditions, the reaction will have ended.

To work up the solid reaction mixture, it can be introduced in water and the resulting mixture be acidified. The 2,4-dihydroxybenzoic acid which precipitates can then be separated off and dried.

It is also possible to extract the solid reaction mixture with lower alcohols, such as methanol, ethanol or isopropanol, at an extraction temperature of from room temperature to the boiling point of the particular extractant used. After the extractant has been removed, the result obtained is a mixture of the sodium and potassium salt of 2,4-dihydroxybenzoic acid, which may either be used as such or be converted into the free acid by acidification. The extraction residue largely comprises sodium bicarbonate and potassium bicarbonate and/or carbonate and, after drying, may be used again in the solid-phase reaction.

It is surprising that the process according to the invention, which may be carried out not only continuously but also batchwise, permits the preparation of 2,4-dihydroxybenzoic acid in the presence of sodium bicarbonate and/or carbonate although this was considered impossible by the prior art.

It is also surprising that the mixture of the sodium and potassium salts of 2,4-dihydroxybenzoic acid can be extracted from the reaction mixture by means of lower alcohols.

2,4-Dihydroxybenzoic acid is a useful intermediate for preparing UV absorbers.

The following Examples will illustrate the invention in more detail:

EXAMPLE 1

A 7-1 solids mixer was charged with 1 kg of potassium bicarbonate, 2 kg of sodium bicarbonate and 700 g of resorcinol, and the contents were heated with mixing to 110° C. in a stream of carbon dioxide. After 3 hours, the contents were cooled with mixing, the pulverulent product (2.77 kg) was introduced into 10 l of water, and the mixture was brought to pH 3 with concentrated hydrochloric acid. Filtering off with suction and drying left 589 g (60%) of 2,4-dihydroxybenzoic acid; purity (HPLC): 99.1%.

EXAMPLE 2

A 7-1 solids mixer was charged with 1 kg of potassium bicarbonate, 2 kg of sodium bicarbonate and 550 g of resorcinol, and the contents were heated with mixing to 110° C. in a stream of carbon dioxide. After 3 hours, the contents were cooled with mixing, the pulverulent product (2.66 kg) was introduced into 6.7 l of water, and the mixture was brought to pH 3 with concentrated hydrochloric acid. Filtering off with suction and drying left 563 g (73%) of 2,4-dihydroxybenzoic acid; purity (HPLC): 99.3%.

EXAMPLE 3

A 7-l solids mixer was charged with 1.5 kg of potassium bicarbonate, 1.5 kg of sodium bicarbonate and 550 g of resorcinol, and the contents were heated with mixing to 110° C. in a stream of carbon dioxide. After 3 hours, the contents were cooled with mixing, the pulverulent product (2.93 kg) was introduced into 10 l of water, and the mixture was brought to pH 3 with concentrated hydrochloric acid. Filtering off with suction and drying left 575 g (75%) of 2,4-dihydroxybenzoic acid; purity (HPLC): 98.3%.

EXAMPLE 4

A 7-l solids mixer was charged with 1 kg of potassium bicarbonate, 2 kg of sodium bicarbonate and 550 g of resorcinol and heated with mixing to 110° C. in a stream of carbon dioxide After 3 hours, the contents were cooled down with mixing, the pulverulent mixture was introduced into 4 l of methanol, and the mixture was refluxed for 1 hour with stirring. The residue was filtered off with suction and dried (1.25 kg). The filtrate was concentrated, and the resulting residue was taken up with water and brought to pH 3. Filtering off with suction and drying left 216 g of 2,4-dihydroxybenzoic acid, purity (HPLC): 99.7%.

EXAMPLE 5

A 35-l solids mixer was charged with 10 kg of sodium bicarbonate, 5 kg of potassium bicarbonate and 3.3 kg of resorcinol and heated with mixing to 120° C. in a stream of carbon dioxide. After 3 hours the contents were cooled down with mixing, and 28 l of water were added. The hot suspension at 60° C. was then discharged and brought to pH 3 at room temperature with 20 kg of concentrated hydrochloric acid. The suspension was cooled to 10–15° C. and filtered on a filter press, and the filter residue was washed with water and dried, leaving 4.1 kg (81%) of 2,4-dihydroxybenzoic acid; purity (HPLC): 99.5%.

We claim:

1. A process for preparing 2,4-dihydroxybenzoic acid in a solids mixer by reacting resorcinol with an alkali metal bicarbonate, alkali metal carbonate or a mixture thereof in a carbon dioxide atmosphere, which comprises using as the alkali metal bicarbonate or alkali metal carbonate a mixture of the corresponding sodium salts and 20–60% of the potassium salts.

2. A process as claimed in claim 1, wherein a mixture of sodium bicarbonate and potassium bicarbonate is used.

3. A process as claimed in claim 1, wherein the reaction is carried out at from 80 to 140° C.

4. A process as claimed in claim 1, wherein the reaction is carried out under atmospheric pressure.

* * * * *